United States Patent [19]

Dodd et al.

[11] 4,418,005

[45] Nov. 29, 1983

[54] PRESSURE ACTIVATION OF MAGNESIUM OXIDE CATALYSTS

[75] Inventors: John R. Dodd; Daniel H. Ralston, both of Ponca City, Okla.

[73] Assignee: Conoco Inc., Ponca City, Okla.

[21] Appl. No.: 392,494

[22] Filed: Jun. 28, 1982

[51] Int. Cl.³ .......................... B01J 27/02; B01J 21/10
[52] U.S. Cl. ...................................... 502/217; 502/340
[58] Field of Search ................................ 252/440, 475

[56] References Cited

U.S. PATENT DOCUMENTS

| | | | |
|---|---|---|---|
| 3,338,972 | 8/1967 | Young | 252/475 X |
| 3,446,856 | 5/1969 | Hamilton | 568/804 X |
| 3,479,410 | 11/1969 | Hamilton | 568/747 X |
| 3,873,628 | 3/1975 | Sorge | 568/804 |
| 3,959,394 | 5/1976 | Tasaka et al. | 252/475 X |
| 3,972,836 | 8/1976 | Sorge | 252/475 X |
| 3,974,229 | 8/1976 | Sorge | 568/804 |
| 4,093,536 | 6/1978 | Heckelsberg | 252/475 X |
| 4,258,220 | 3/1981 | Leach et al. | 568/752 X |
| 4,269,735 | 5/1981 | Leach | 252/457 X |
| 4,283,573 | 8/1981 | Young | 568/804 X |

FOREIGN PATENT DOCUMENTS 32974  8/1981  European Pat. Off. ............. 502/217

*Primary Examiner*—William G. Wright
*Attorney, Agent, or Firm*—Cortlan R. Schupbach, Jr.

[57] ABSTRACT

A titanium oxide/magnesium sulfate/magnesium oxide catalyst which is an ortho-selective methylation catalyst can be made to exhibit higher conversion and activity index for phenol methylation by the application of pressure. The pressure can be applied throughout the methylation period or can be applied for a short time at the beginning of the methylation period and then ceased, while higher activity continues. The pressure activation effects are assisted by the presence of phenol, methanol and/or water.

8 Claims, No Drawings

PRESSURE ACTIVATION OF MAGNESIUM OXIDE CATALYSTS

This invention relates to methylation of phenols. More specifically, this invention relates to a method for activating and maintaining activity in magnesium oxide catalysts used to methylate phenols.

Methylation of phenols over magnesium oxide catalysts is well known in the art as taught in U.S. Pat. No. 3,479,410. Various improvements have been made in magnesium oxide catalysts to enable them to function more efficiently or to provide more specific product distributions depending on the reaction conditions and catalyst promoters used. Representative but non-exhaustive examples of art representing such improvements are U.S. Pat. Nos. 4,283,574; 4,269,735; 4,258,220; and 3,974,229.

Thus there are many catalyst which form orthomethylated products in the methylation of phenol in vapor phase. Magnesium oxide itself is a useful catalyst as described in U.S. Pat. No. 3,446,856, but requires high temperatures in the range of 475° C. to 600° C. In this temperature range catalyst life is short and methanol decomposition is high. Attempts to overcome this short catalyst life were described in U.S. Pat. No. 3,873,628 wherein manganese sulfate on magnesium oxide was used.

Prior art catalysts while useful for various reactions have hitherto not been sufficiently reactive, did not develop high enough surface area and crush strength, or required reactions be carried out at such high temperatures that the catalyst life was short while product and feedstream decomposition was high. U.S. Pat. No. 4,269,735 describes an active magnesium oxide catalyst containing amorphous titanium, uranium, chromium or zirconium ions together with sulfate ions as an effective promoter in catalysts for this reaction.

However, as in any reaction, eventual fouling of the catalyst and lowered reaction rates and/or product shifts to undesirable components occur over a period of time, even though the period of time is much longer than prior art catalysts. It would be of great benefit to provide a method for making the catalyst even more active prior to insertion into the reactor such that useful life is extended. Providing a method for reactivating a catalyst in the reactor during a methylation reaction to extend catalyst life would be even more preferable, especially by devising a method whereby the two procedures could be used in combination to greatly increase catalyst activity as the catalyst gradually becomes less active during methylation reactions.

It is therefore an object of the present invention to provide a method for activating magnesium oxide catalysts and provide higher catalyst activity. Other objects will become apparent to those skilled in this art as the description proceeds.

We have now discovered that the application of pressure to a magnesium oxide catalyst, particularly ortho-selective methylation catalysts, prior to use in a methylation reaction serves to activate the catalyst. Subsequent phenolics methylation after pressure activation shows that conversion and activity index are higher and that the ortho-cresol/2,6-xylenol ratio is lower than before the pressure activation when compared to a control run. Pressure activation does not result in any significant decline in selectivity to ortho-methylated phenols. In addition, once carried out and used in a methylation reaction, and when deactivation begins to occur, higher pressures can again be applied to the reactor to reactivate the catalyst for short periods of time. Eventually, catalyst inactivity will result, but the application of intermittant pressure above that normally used during such a reaction run allows catalyst activity to increase and remain higher for substantial periods of time, even after the pressure is returned to normal methylation conditions.

As with essentially all heterogeneous catalysts used under vapor phase conditions, the useful lifetime of magnesium oxide-based catalysts is limited due to coking and/or tar formation on the catalysts. Therefore the catalysts must be periodically regenerated or replaced. Replacement is expensive and requires much plant down time. In the present invention such catalyst can be reactivated without the necessity of complete reactor shutdown. Thus catalyst activity can be regenerated such that the effective life of the catalyst is increased.

In carrying out the process of the present invention, the catalyst can be activated prior to use in the methylation reaction by subjecting the catalyst to pressures of from about 10 to about 2000 pounds per square inch gauge (psig), although it is preferred that the catalyst be subjected to pressures of from 30 to 1000 pounds and the most preferred pressure range is from about 80 to about 1000 psig.

The catalysts are subjected to such pressure for periods of time ranging from about 2 to 1000 hours. However, it is preferred that pressure be maintained on the catalyst for periods of time ranging from about 10 to about 100 hours and from about 20 to about 50 hours is most preferred.

The temperature during catalyst activation should range from about 150° C. to about 500° C., although temperatures of from about 300° C. to about 480° C. are preferred. The most preferred temperatures are from about 450° C. to about 480° C.

This pressure treatment prior to use in a phenol methylation reaction can be useful for any magnesium oxide-based catalyst. However, it is preferred that this pressure treatment be utilized on magnesium oxide-based catalysts containing promoting metal ions. The process of the present invention is most useful on a magnesium oxide-based catalyst containing both titanium and sulfate ions.

Once the activated catalyst has been used in a methylation reaction and activity begins to decrease because of coking and/or catalyst pore blockage, the catalyst can be activated in situ during a methylation run by utilizing the proper temperature, pressure and feed condition. In such an in situ activation, it is necessary that the feed be a mixture of alkanol/phenol or alkanol/water/phenol. However, it is preferred that the feed be a methanol, phenol, water feed containing from 1:1 to 10:1 mole ratio of methanol to phenol and from 1 to 20 weight percent water. Activation will be most successful when the feed is methanol/phenol/water feed containing from about 3:1 to about 7:1 moles ratio of methanol to phenol, and from about 3 to about 10 weight percent water. The latter feed is most preferred.

During such in situ activations, the liquid hourly space velocity (LHSV) of the feed should range from about 0.5 to about 5.0, but from about 0.5 to about 2.0 is preferred. The most preferred LSHV is from about 1.0 to about 1.5.

When utilizing in situ activations, higher pressures than normally encountered during alkylation reactions should be used. Although some activation will occur at about 40 psig, it is preferred that pressures of at least 80 psig be utilized during the in situ activation. Other than this slightly higher pressure necessary during in situ activation, pressure ranges are as described for the non-in situ activation.

The invention is more concretely described with reference to the examples below wherein all parts and percentages are by weight unless otherwise specified. The examples are provided to illustrate the present invention and not to limit it.

EXAMPLE 1

The effect of pressure treatment during methylation upon the activity of titanium dioxide/magnesium sulfate/magnesium oxide ($TiO_2/MgSO_4/MgO$) catalysts was determined. The experiment was begun after the catalyst had been used for 138 hours following two catalyst regenerations. Product stream samples were obtained at 1 LHSV, 460° C. and 0 psig. Thereafter, the reactor pressure was raised to 40 psig, held at this pressure for 24.3 hours, and then brought back to 0 psig. Samples of the product stream were taken periodically with time at 1 LHSV, 460°–462° C., and 0 psig. A constant set point of the reactor controller was maintained throughout this experiment. The feed contained a 5:1 mole ratio of methanol to phenol and 9.1 weight percent water and was used throughout the experiment. The catalyst used was ⅛-inch pellets of $TiO_2/MgSO_4/MgO$ experimental catalyst.

In the table, the elapsed time is the time since the start of the experiment. The elapsed time equalled zero at the time that sample 1 was taken, prior to raising the pressure to 40 psig. This time was such that the catalyst had been on stream for 138 hours following two catalyst regenerations with accumulative run time of 751 hours. Sampling time is the time the given sample was taken after pressure reduction with T=0 being the time at which the pressure was reduced from 40 psig to 0 psig.

The following terms define the table. Act. Index is the activity index which is defined as total moles of methanol incorporated in the phenolics per mole of phenolic converted in one reactor pass during the methylation. The term PhOH conv. is the mole percent phenol conversion. Sel(0+26) is either the weight percent or mole percent of (of combined ortho-cresol and 2,6-xylenol) selectivity. The R's are ratios of components in the product stream relative to 2,6-xylenol (=1). $R_1$ is the phenol/2,6-xylenol ratio, $R_2$ is the ortho-cresol/2,6-xylenol ratio, $R_3$ is the (2,4-xylenol+2,4,6-trimethylphenol)/2,6-xylenol ratio, and $R_4$ is the (total anisoles)/2,6-xylenol ratio. In all cases the 2,6-xylenol to 2,6-xylenol ratio is 1 by definition.

The total anisoles is the weight percent of anisoles in the phenolic mixture on a methanol-water-free basis and includes anisole, ortho-methylanisole and 2,6-dimethylanisole. The term Σ24+246 is the total weight percent of 2,4-xylenol and 2,4,6-trimethylphenol in the phenolic mixture, again on a methanol-water-free basis.

TABLE 1

| | | | Pressure Activation of $TiO_2/MgSO_4/MgO$ Catalyst | | | | | | | | | |
|---|---|---|---|---|---|---|---|---|---|---|---|---|
| Sample | Elapsed Time (hrs.) | Sampling Time (hrs.) | Act Index | PhOH Conv. | Sel (o + 26) | Sel (o + 26) | $R_1$ | $R_2$ | $R_3$ | $R_4$ | ε Anis (w/o) | ε 24 + 246 (w/o) |
| 1 | 0 | | 0.78 | 57.9 | 95.9 | 96.2 | 1.89 | 2.00 | .09 | .04 | .79 | 1.79 |
| 2 | 25.3 | 1.0 | 1.01 | 65.2 | 93.5 | 94.1 | .88 | .90 | .10 | .03 | 1.12 | 3.44 |
| 3 | 26.3 | 2.0 | 0.98 | 64.1 | 93.6 | 94.2 | .96 | .96 | .10 | .03 | 1.05 | 3.34 |
| 4 | 28.6 | 4.3 | 0.95 | 61.7 | 93.8 | 94.4 | 1.05 | .95 | .10 | .03 | 1.02 | 3.09 |
| 5 | 31.8 | 6.5 | 0.92 | 59.3 | 93.6 | 94.3 | 1.14 | .92 | .10 | .03 | .89 | 2.50 |
| 6 | 47 | 22.7 | 0.83 | 55.2 | 94.4 | 94.9 | 1.45 | 1.06 | .09 | .03 | .89 | 2.50 |

The reaction was carried out in a continuous methylation reactor (¾-inch i.d. by 14 inches long) equipped with a furnace and temperature controller, a preheater to vaporize the reactants, a pressure regulator and a metering pump to pump feed into the reactor at a constant rate. A 25 milliliter (ml) catalyst bed was used which was centered in the reactor using glass beads as a filler. The catalyst was a titanium dioxide/magnesium sulfate/magnesium oxide catalyst used as ⅛-inch pellets. The catalyst had been regenerated twice using air, steam and heat treatment and had accumulative run time of 751 hours prior to the beginning of this experiment.

Comparisons of selected reaction parameters under comparable conditions before and after pressurized treatment of the catalyst are set forth in Table 1. The pressure treatment resulted in an increase in activity for this catalyst from that observed prior to the pressure treatment as determined by increases in the activity index and phenol conversion and decreases in the phenol/2,6-xylenol and ortho-cresol/2,6-xylenol ratios. Only a very slight and minor decrease in selectivity accompanying the activity increase occurred. There were also slight increases in the levels of total anisoles and total (2,4-xylenol plus 2,4,6-trimethylphenol) streams.

EXAMPLE 2

The effect of high pressure treatment (1000 pounds per square inch gauge for 24 hours) upon the activity of titanium dioxide/magnesium sulfate/magnesium oxide catalyst was determined. A methylation run was carried out using pressurized treatment and a separate control run was carried out without pressurized treatment. The results are set forth in Table 2 wherein C was a control run in which conditions were kept constant at 460° C., 1 LHSV and 0 psig. The term P designates a pressure activation experiment in which the conditions were the same as the control run for 0 to 24 hours, the pressure thereafter raised to 1000 psig from 24 to 48 hours, and after 48 hours the pressure was again dropped to 0 psig. The feed was a 5:1 mole ratio of methanol to phenol and 9.1 weight percent water. All other terms are the same as defined in Example 1. The catalyst used was an experimental $TiO_2/MgSO_4/MgO$ catalyst.

The reactions were carried out in two identical continuous methylation reactors, (0.39 inches i.d. by 28 inches long) each equipped with a tubular furnace and temperature controller to maintain the reactor at a constant elevated temperature. The reactions were equipped with a preheater to vaporize the reactants, a pressure regulator and a metering pump to pump feed into the reactor at a constant rate. A 25-ml catalyst bed was used in each case which was centered in the reactor using glass beads as filler. The catalyst used in all reactions for this experiment was in the form of 8-14 mesh particles.

TABLE 2

Pressure Activation of $TiO_2/MgSO_4/MgO$ Catalyst

| Run | Time (hrs.) | T (°C.) | P (psig) | LHSV $(hr^{-1})$ | Act Index | PhOh Conv. (m/o) | Sel (o + 26) (w/o) | Sel (o + 26) (m/o) | $R_1$ | $R_2$ | $R_3$ | $R_4$ | $R_5$ | $\epsilon$ anis (a/o) | $\epsilon$ 24 + 246 (a/o) |
|---|---|---|---|---|---|---|---|---|---|---|---|---|---|---|---|
| C | 63 | 459 | 0 | 1.0 | 0.70 | 56.3 | 94.1 | 94.7 | 3.27 | 3.71 | 1.00 | .18 | .10 | 1.18 | 2.17 |
| P | 65.5 | 461 | 0 | 1.0 | 0.78 | 62.2 | 93.6 | 94.2 | 2.51 | 3.58 | 1.00 | .20 | .12 | 1.57 | 2.64 |
| C | 88.5 | 460 | 0 | 1.0 | 0.58 | 48.9 | 96.5 | 96.8 | 4.85 | 4.27 | 1.00 | .09 | .10 | .93 | .90 |
| P | 86.5 | 461 | 0 | 1.0 | 0.73 | 59.5 | 93.7 | 94.3 | 3.03 | 3.93 | 1.00 | .22 | .11 | 1.35 | 2.62 |

Experiments carried out with pressure treatment of the catalyst during methylation served to increase the activity of the catalys as signified by higher values of the activity index and phenol conversion and lower values of the phenol/2,6-xylenol and ortho-cresol/2,6-xylenol ratios relative to the non-pressurized control run. Pressures as high as 1000 psig or higher are therefore useful in activating the catalysts. Only a slight decrease in selectivity accompanied the increased activity after pressure treatment. There were slight increases in the level of total anisoles and total (2,4-xylenol+2,4,6-trimethylphenols).

EXAMPLE 3

A sample (100 g) of calcined $TiO_2/MgSO_4$ catalyst is charged to an autoclave. A methanol/phenol/water solution (200 ml) is added which contains a 5:1 mole ratio of methanol to phenol and 9 weight percent (w/o) water. The mixture is heated at 400° C. with pressures in excess of 50 psig for 10 hours. The mixture is cooled, filtered and rinsed with methanol. The catalyst is then dried in vacuo at 150° C. for 2 hours. The resulting activated $TiO_2/MgSO_4/MgO$ catalyst (25 ml) is charged to a continuous tubular methylation reactor and used for phenol methylation under typical conditions (460° C., 1. LHSV, 0-60 psig, feed=5:1 methanol to phenol mole ratio+9 w/o of water). The catalyst exhibits enhanced activity for phenol methylation over otherwise identical catalyst without the activation treatment.

While certain embodiments and details have been shown for the purpose of illustrating this invention, it will be apparent to those skilled in this art that various changes and modifications may be made herein without departing from the spirit or scope of the invention.

We claim:

1. A method for increasing the activity of magnesium oxide-based alkylation catalysts comprising, prior to use in an alkylation reaction, pressure treating the catalysts for a time of at least 2 hours at pressures of at least 40 pounds per square inch gauge and a temperature of at least 150° C.

2. A method as described in claim 1 wherein the catalyst is a metal ion promoted magnesium oxide catalyst.

3. A method as described in claim 2 where in addition the catalyst contains sulfate ion.

4. A method as described in claim 1 wherein the catalyst is treated at a temperature of at least 300° C. for at least 10 hours.

5. A method as described in claim 4 wherein the catalyst is treated at pressures of from about 80 to about 1000 psig.

6. A method as described in claim 5 wherein reactivation is carried out during a methylation reaction by altering reaction conditions to a pressure of at least 80 psig for a time necessary to achieve catalyst reactivation.

7. A method as described in claim 6 wherein the catalyst is treated at a liquid hourly space velocity of at least 0.5 with a material selected from the group consisting of phenol, methanol, water, or mixtures of these.

8. A method as described in claim 7 wherein the methylation reaction is carried out under pressures of less than 80 psig after catalyst reactivation.

* * * * *